United States Patent [19]

Hung et al.

[11] Patent Number: 5,198,556
[45] Date of Patent: Mar. 30, 1993

[54] DIOXOLANE-CONTAINING FLUOROEPOXIDES

[75] Inventors: Ming-Hong Hung; Shlomo Rozen, both of Wilmington, Del.

[73] Assignee: E. I. Du Pont de Nemours and Company, Wilmington, Del.

[21] Appl. No.: 746,241

[22] Filed: Aug. 15, 1991

[51] Int. Cl.$^5$ .................. C07D 317/10; C07D 317/42
[52] U.S. Cl. .................................. 549/448; 549/455; 549/472
[58] Field of Search .................. 549/448, 455, 472

[56] References Cited

U.S. PATENT DOCUMENTS 3,086,025 4/1963 Tinsley et al. ........................ 549/448
4,393,227 7/1983 Squire ................................ 549/455

Primary Examiner—Alan L. Rotman
Assistant Examiner—Ba K. Trinh
Attorney, Agent, or Firm—Barbara C. Siegell

[57] ABSTRACT

The present invention concerns novel dioxolane containing fluoroepoxides that are useful as curing materials, adhesives lubricants and coatings.

10 Claims, No Drawings

DIOXOLANE-CONTAINING FLUOROEPOXIDES

BACKGROUND OF THE INVENTION

1. Field of the Invention

The present invention concerns novel dioxolane-containing fluoroepoxides. Epoxides are useful as lubricating materials, curing materials, adhesives and coatings.

2. Technical Review

U.S. Pat. No. 3,324,144 discloses a process for preparing a 2,2-bis(polyfluoroalkyl)-1,3-dioxolane.

U.S. Pat. No. 3,879,430 discloses fluorinated diglycidyl ethers having the formula:

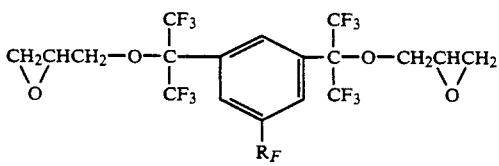

wherein $R_F$ is $CF_3(CF_2)_x$, X being an integer from 2 to 10.

U.S. Pat. No. 3,720,639 discloses the formation of a fluorinated polyol from the polymerization of a diglycidyl ether with a fluorinated dihydroxyhydrocarbon.

Sheng Yen Lee and James R. Griffith, Fluoroepoxy Resin for Moisture Vapor Barrier Coating and Other Applications, I and EC Product Research and Development, December 1986, 572-577, American Chemical Society.

Howard E. Simmons and Douglas W. Wiley, Fluoroketones I, Journal of the American Chemical Society, vol. 82, pages 2288-2296 (1960) disclose fluoroketones as intermediates for the synthesis of fluorine-containing structures. Fluoroketones are reacted with diazomethane to give high yields of stable epoxides and condensed readily with active methylene compounds and metallic acetylides.

M. H. Hung et al., J. Org. Chem., 56, p. 3187 (1991) discloses the epoxidation of fluorinated olefins using $F_2/H_2O/CH_3CN$ reagent.

None of the aforementioned references disclose the compositions claimed herein.

SUMMARY OF THE INVENTION

This invention provides dioxolane-containing fluoroepoxides of structure 1:

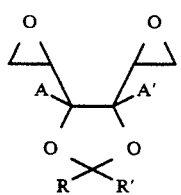

wherein each A and A' is independently F or $CF_3$, provided, however, that both A and A' are not concurrently $CF_3$.

R and R' are independently F, $C_1$ to $C_3$ fluoroalkyl or chlorofluoroalkyl having at least one fluorine substituent, and Structure 2:

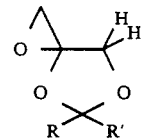

wherein:

R and R' are independently F, $C_1$ to $C_3$ fluoroalkyl or chlorofluoroalkyl with at least one fluorine substituent.

A preferred embodiment for structure 1 is where A and A' are both F and R and R' are both $CF_3$.

DETAILED DESCRIPTION OF THE INVENTION

The invention concerns dioxolane-containing fluoroepoxides, as defined above, that are produced by the epoxidation of olefins.

Epoxidation can be carried out using various processes. The epoxidation of olefins on a large scale is known. See Kirk-Othmer Encyclopedia of Chemical Technology, 3rd ED., vol. 9, John Wiley and Sons, New York, 1980, p. 251-166. Various methods of epoxidating fluorinated olefins are disclosed by P. Tarrant, et al., in Fluorine Chemistry Reviews, vol. 5, Marcel Dekker, Inc., New York, 1971, p. 77-85. Most of these methods involve more than one step, unlike the present direct epoxidation procedure.

Direct epoxidation of fluorinated olefins is carried out by first creating an oxidizing reagent by passing elemental fluorine through a mixture of acetonitrile and water, and then contacting a fluorine containing olefin with the oxidizing solution to yield a desired epoxide. Suitable fluorinated olefins for use in such an epoxidation process include $ZCH=CH_2$ and $YCH_2CH=CH_2$ wherein Z is $ACF_2—$, or perfluoroalkyl, and Y is $ABCF—$ or perfluoroalkyl; A is fluorine, hydrocarbyl, or substituted hydrocarbyl and B is fluorine or perfluoroalkyl. Suitable substituents, when A is a substituted hydrocarbyl, include the vinyl group, $CH_2=CH—$ and/or any other substituent that is inert under the reaction conditions. When the vinyl group, $H_2C=CH—$ is present, it too will be epoxidized, assuming that enough oxidizing reagent is present. The process is carried out at a temperature range from $-15°$ C. to about 30° C. Preferably, the reaction is carried out from 0° C. to 25° C. Reaction times can vary from about one minute to three or more hours. The desired product may be isolated by extraction, followed by distillation or evaporation of the solvent.

The starting material for Structure 1 where A and A' are both F and R and R, are both $CF_3$, is compound X:

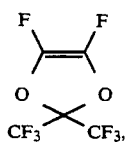

described in U.S. Pat. No. 3,865,845, which is incorporated herein by reference. Compound X is then converted to a diolefin precursor which is converted to Structure 1.

The diolefin precursor of Structure 1, where A and A' and R and R' are all F, disclosed in U.S. Pat. No.

4,399,264, which is incorporated herein by reference, can be produced from compound Y:

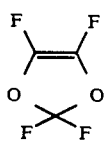

The diolefin precursor of Structure 1, where A or A' is CF$_3$ and the other A or A' is F, and R and R' are both CF$_3$, can be produced from compound Z:

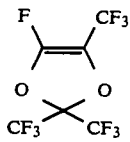

which is known. (See Ming-H, Hung and Paul R. Resnick, Journal of the American Chemical Society, 112, 9671–9672 [1990]).

The direct epoxidation of the dioxolane olefins, used to produce the present dioxolane-containing epoxides, is believed to be based on the ability of fluorine to react with water and acetonitrile resulting in an oxidizing solution which is able to epoxidize double bonds. Unlike other direct epoxidations, this method allows the direct formation of oxiranes, even with very electron deficient olefins such as fluorine containing olefins.

The fluorine containing epoxides are useful as lubricants, curing materials, adhesives and coatings.

EXAMPLES

General Procedure For The Epoxidation of Dioxolane Olefins

When fluorine, diluted with nitrogen, is passed through a cold (−10° C.) mixture of acetonitrile-water, an oxidizing solution is formed that is stable for several hours at temperatures of up to 25° C. The reagent reacts quickly and smoothly with several types of olefins to produce epoxides. In the case of the bis-trifluoromethyl fluoro-dioxolane olefins, at least two mole/equiv of the oxidizing reagent are used and the reaction takes 2 to 5 minutes at room temperature. This usually results in 85%–95% yield of the epoxide in practically quantitative conversion.

In the Examples below efforts were made to epoxidize the cis and trans bis-trifluoromethyl difluoro-oxolone di-olefin 3, as well as the monoolefinic derivative 4, to the corresponding cis and trans bis-epoxides 5 and the mono-epoxide 6. These epoxidations are shown as follows:

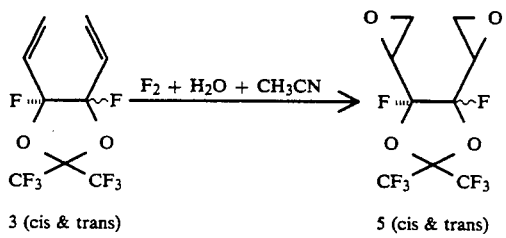

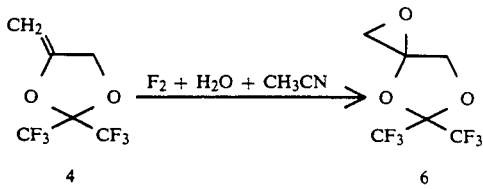

General Procedure For Working With Fluorine

Fluorine is a strong oxidizer and a very corrosive material. An appropriate vacuum line made from copper or monel in a well ventilated area should be constructed for working with this element. The reactions themselves can be carried out in glass vessels with elementary precautions.

General Procedure For Producing The Oxidizing Reagent

Mixtures of 10%–15% F$_2$, diluted with nitrogen, were used in this work. The gas mixtures were prepared in a secondary container before the reaction was started. This mixture was then passed in a rate of about 400 ml per minute through a cold (−10° C.) and vigorously stirred mixture of 400 ml CH$_3$CN and 40 ml H$_2$O. The formation of the oxidizing power was monitored by reacting aliquots with acidic aqueous solution of KI. The liberated iodine was then titrated with thiosulfate. Concentrations of more then a mol/liter oxidizing reagent can be formed.

General Epoxidation Procedure

An appropriate amount of olefin (usually up to half the molar amount of the oxidizing reagent) is dissolved in about 50 ml of CH$_2$Cl$_2$ cooled to 0° C. and added in one portion to the reaction vessel in which the oxidizing agent has been prepared. The cooling bath is removed and the reaction is left for 5 minutes. It is then neutralized with saturated aqueous sodium bicarbonate solution and poured into 1.5 liter water, extracted with CFCl$_3$ and washed with aqueous NaHCO$_3$ and water until neutral. The organic layer is dried over MgSO$_4$, and the solvent distilled with distillation column. The crude product is usually distilled under reduced pressure.

Epoxidation of the trans-diolefin 3

Trans-olefin 3 (28 g, 54 mmol) in CH$_2$Cl$_2$ (30 ml) was added to a solution containing 130 mmoles of the oxidizing agent. After 10 minutes the reaction was worked up as described above. After removal of the solvent the reaction mixture was distilled to give 24.1 g (77% yield) of the trans-epoxide 5 as a clear, colorless liquid, bp. 81° C./5mm. $^1$H NMR (CDCl$_3$): δ3.42 (m, 2H), 3.10, 3.07, 2.90 (m,2H), 2.96 (m, 2H); $^{19}$F NMR (CDCl$_3$): −80.2, −80.4 (2m, 6F), -121.9 (m, 1F), −122.3, −128.4 (2m, 1F); Anal. Calc. for C$_9$H$_6$F$_8$O$_4$: C: 32.73, H: 1.83, F: 46.05; Found: C: 32.70, H: 1.61, F: 45.82. Mass for [M+H]: Calc: 331.02166; Found: 331.02506.

EXAMPLE 2

Epoxidation of the cis- diolefin 3

Cis-olefin 3 (1.0 g, 3.36 mmol) in CH$_2$Cl$_2$ (30 ml) was added to a solution containing 160 mmoles of the oxidizing agent. The reaction was worked up as described above. After distillation of the solvent two diastereoisomers of cis-5 were obtained in 81% yield (0.9 g).

EXAMPLE 3

Epoxidation of the Mono-Olefin 4

Olefin 4 (19 g, 85 mmol) in CH2Cl2 (40 ml) was added to a solution containing 200 mmoles of the oxidizing agent. After 5 minutes the reaction was worked up as described above. After distillation of the solvent the reaction mixture was distilled and the main fraction which was identified as the mono-epoxide 6, bp. 55° C/2mm, yield 94%; IR =2980, 2920, 1520, 1330, 1220, cm$^{-1}$; $^1$H NMR (CDCl3): δ4.56 (d, J=10 Hz, 1H), 4.33 (d, J=10 Hz, 1H), 3.42 (d, J=2.7 Hz, 1H), 3.04 (d, J=2.7 Hz, 1H); $^{19}$F NMR (CDCl3): −81.0 (q, J=8.0 Hz, 3F), −81.5 (q, J=8.0 Hz, 3F); Anal. Calc. for $C_6H_4F_6O_3$: C: 30.27, H: 1.69, F: 47.88; Found: C: 30.08, H: 1.90, F: 47.55. Mass for [M]: Calc: 238.0064; Found: 238.0098).

EXPERIMENT 1

Synthesis of 2,2-bis(trifluoromethyl)-4-bromomethyl-1,3-dioxolane 7

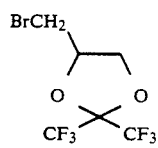

7

This compound was prepared from epibromohydrin and hexafluoroacetone (HFA) (1:1 mole ratio) in the presence of catalytic amounts of tetrabutylammonium bromide and water at 125° C. in 95% isolated yield. Compound 7 has a boiling point 56° C./2 mm. $^1$H NMR (neat): δ4.88 (m, 1H), 4.73 (t, J =7.5 Hz, 1H), 4.22 (t, J=7.5 Hz, 1H), 3.60 (m, 2H); 19F NMR (neat): −80.5 (q, J=8.5 Hz, 3F), −81.0 (q, J=8.5 Hz, 3F). Anal. Calc. for $C_6H_5BrF_6O_2$: C: 23.78, H: 1.66, Br: 26.37, F: 37.62; Found: C: 23.91, H: 1.64, Br: 26.87, F: 37.84.

EXPERIMENT 2

Synthesis of 2,2-bis(trifluoromethyl)-4-methylene-1,3-dioxolane 4

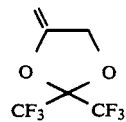

4

Compound 7 obtained from above reaction (30.3 g) was mixed with 10M KOH (60 ml) and phase transfer catalyst (note) (7.13 g), stirred at ambient temperature for 16 hours, the bottom organic layer was separated, washed with water and distilled to give 4 as a clear, colorless liquid; yield 18 g (81%); bp. 85° C. or 47° C./240mm. 1H NMR (neat): δ4.60 (m, 3H), 4.10 (m, 1H); $^{19}$F NMR (neat): −82.2 (s). $^{13}$C NMR (CDCl3): 69.1, 83.9, 153.2 (C=CH2), 101.5 (4° C.), 120.0 (q, $J_{c-F}$=288 Hz, CF3); Anal. Calc. for $C_6H_4F_6O_2$: C: 32.45, H: 1.82, F: 51.33; Found: C: 31.96, H: 1.81, F: 51.45. IR: 1710 cm$^{-1}$, 1682 cm$^1$, 840 cm$^{-1}$. Note: [CH3CH(OH)CH2-]2—N(CH2C6H5)(C12H25)Cl (60% w/w aqueous solution obtained from E. I. du Pont de Nemours and Company) was used as the phase transfer catalyst.

The reactions below illustrate Experiments 3, 4, and 5.

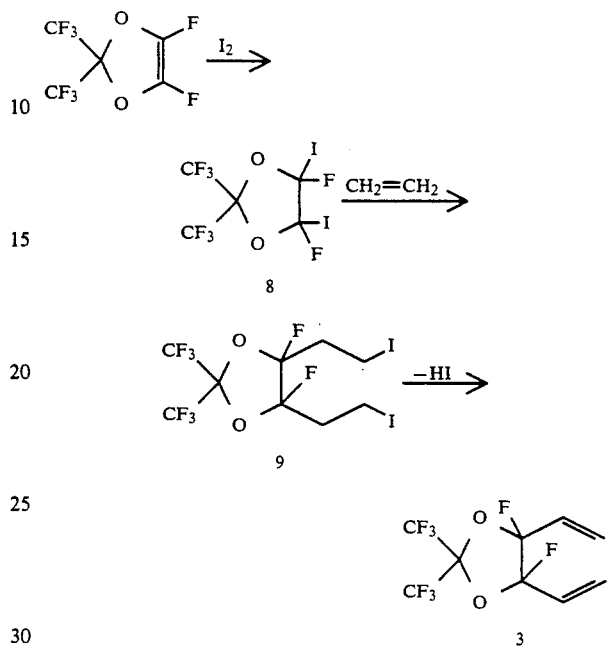

EXPERIMENT 3

Preparation of 2.2-bis(trifluoromethyl)-4,5-difluoro-4,5-diiodo-1,3-dioxolane 8

Perfluoro-2,2-dimethyl-1,3-dioxole (48.8 g, 0.2 mole) (U.S. Pat. No. 3,865,845) was mixed with iodine (70 g, 0.276 mole) in tetrahydrofuran solvent (20 ml) in a dried round-bottom flask. The reaction mixture was heated up slowly to 70° C. The reaction was monitored by gas chromatography and stopped when the conversion of the substrate reached completion. The product was distilled out from the reaction mixture, washed with saturated sodium thiosulfate aqueous solution and distilled again to give the desired product 69.4 g (70% yield) as a clear liquid, bp. 70° C./40–50 mm. This product is a trans/cis isomeric mixture. $^{19}$F NMR(Neat): −26.8 (m, trans); −39.5 (m, cis).

EXPERIMENT 4

Preparation of 2,2-bis(trifluoromethyl)-4,5-difluoro-4,5-di(2-iodoethyl)-1,3-dioxolane 9

In a 400 ml stainless steel shaker tube was charged 2,2-bis(trifluoromethyl)-4,5-difluoro-4,5-diiodo-1,3-dioxolane 8 (199.2 g, 0.4 mole) and d-limonene (2.0 g). The tube was sealed, cool-evacuated and charged with ethylene (60 g, 2.14 mole). The tube was sealed and heated at 220° C. for 10 hrs. The tube was then cooled and the product mixture was fractionally distilled to give the desired product (115 g, 52% yield) as a pale-yellow viscous liquid, bp 105° C./0.5 mm. The product was obtained as a trans/cis isomeric mixture. $^{19}$F NMR (Neat): −79.0 (m, 6F), [−105.8 (m, trans); −108.0 (m, br, cis)] (2F total).

EXPERIMENT 5

Preparation of 2,2-bis(trifluoromethyl)-4,5-difluoro-4,5-divinyl-1,3-dioxolane 3

In a flask was charged above compound 9 (95 g, 0.17 mole), 10M KOH (189 ml, 1.89 mole) and phase transfer catalyst (Note) (24.6 g as 60% w/w aqueous solution, 0.034 mole). The reaction mixture was vigorously stirred at ambient temperature for 4 hrs. The bottom organic layer was separated and was further purified by distillation giving 25.0 g (49.3% yield) of the desired Product was obtained as a clear, colorless liquid, bp. 90° C./200 mm.

This product is a trans/cis isomeric mixture. The trans and cis isomers could be separated by distillation on a spinning-band column. $^1$H NMR (CDCl$_3$): $\delta$5.90 (m, 2H), 5.70 (m, 4H) (trans-isomer); 5.76 (m, 4H), 5.58 (m, 2H) (cis-isomer); $^{19}$F NMR (CDCl$_3$): $-80.2$ (m, 6F), $-109.6$ (m, 2F) (trans-isomer); $-80.2$ (m, 3F), $-81.0$ (q, J=8.6 Hz, 3F), $-109.3$ (quintet, J=7.0 Hz, 2F). Note: [CH$_3$CH(OH)CH$_2$]$_2$—N(CH$_2$C$_6$H$_5$)(C$_{12}$H$_{25}$)Cl (60% w/w aqueous solution obtained from E. I. du Pont de Nemours and Company) was used as the phase transfer catalyst.

Although preferred embodiments have been described herein, it is understood that there is no intention to limit the invention to the precise constructions herein disclosed, and it is to be further understood that the right is reserved to all changes coming within the scope of the invention as defined by the appended claims.

We claim:

1. A dioxolane-containing fluoroepoxide of the structure 1,

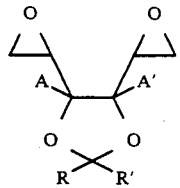

wherein
each A and A' is independently F or CF$_3$, provided that both A and A' are not concurrently CF$_3$;
R and R' are independently F, C$_1$ to C$_3$ fluoroalkyl or chlorofluoroalkyl with at least one fluorine substituent.

2. The fluoroepoxide of claim 1 wherein A is CF$_3$ and A' is F.

3. The fluoroepoxide of claim 1 wherein A and A' are both F.

4. The fluoroepoxide of claim 1 wherein R and R' are both F.

5. The fluoroepoxide of claim 1 wherein R and R' are C$_1$ to C$_3$ fluoroalkyl or chlorofluoroalkyl with at least one fluorine substituent.

6. The fluoroepoxide of claim 1 where R is F and R' is a C$_1$ to C$_3$ fluoroalkyl or chlorofluoroalkyl with at least one fluorine substituent.

7. The fluoroepoxide of claim 2 wherein R and R' are both F.

8. The fluoroepoxide of claim 2 wherein R and R' are both C$_1$ to C$_3$ fluoroalkyl or chlorofluoroalkyl, with at least one fluorine substituent.

9. The fluoroepoxide of claim 2 wherein R is F and R' is C$_1$ to C$_3$ fluoroalkyl or chlorofluoroalkyl, with at least one fluorine substituent.

10. The fluoroepoxide of claim 3 wherein R and R' are both CF$_3$.

* * * * *